US008216205B2

(12) United States Patent
Suzuki et al.

(10) Patent No.: US 8,216,205 B2
(45) Date of Patent: Jul. 10, 2012

(54) DISPOSABLE DIAPER

(75) Inventors: Sachiyo Suzuki, Kagawa-ken (JP); Toshifumi Otsubo, Kagawa-ken (JP)

(73) Assignee: Uni-Charm Corporation, Ehime (JP)

( * ) Notice: Subject to any disclaimer, the term of this patent is extended or adjusted under 35 U.S.C. 154(b) by 25 days.

(21) Appl. No.: 11/056,275

(22) Filed: Feb. 14, 2005

(65) Prior Publication Data

US 2005/0182381 A1 Aug. 18, 2005

(30) Foreign Application Priority Data

Feb. 17, 2004 (JP) .................................. 2004-40231

(51) Int. Cl.
*A61F 13/15* (2006.01)
*A61F 13/20* (2006.01)
(52) U.S. Cl. ........................... 604/385.28; 604/385.24
(58) Field of Classification Search ........ 604/385.24–385.29, 385.1, 385.2, 604/385 R, 385 A, 384, 385.21, 385.01, 385.101, 604/397–98; 128/155–56, 287
See application file for complete search history.

(56) References Cited

U.S. PATENT DOCUMENTS

| 2,110,867 | A | * | 3/1938 | Castles ........................... 428/89 |
| 3,332,828 | A | * | 7/1967 | Faria et al. ..................... 428/17 |
| 3,665,922 | A | * | 5/1972 | Skora ........................... 604/366 |
| 3,666,608 | A | * | 5/1972 | Mattes ........................... 428/81 |
| 4,576,848 | A | * | 3/1986 | Dillon et al. ..................... 428/89 |
| 4,622,253 | A | * | 11/1986 | Levy ............................... 428/91 |
| 4,695,278 | A | | 9/1987 | Lawson |
| 4,895,568 | A | * | 1/1990 | Enloe ........................ 604/385.27 |
| 5,108,820 | A | | 4/1992 | Kaneko et al. |
| 5,167,653 | A | * | 12/1992 | Igaue et al. .............. 604/385.04 |
| 5,295,986 | A | * | 3/1994 | Zehner et al. ............. 604/385.25 |
| 5,334,176 | A | | 8/1994 | Buenger et al. |
| 5,460,622 | A | * | 10/1995 | Dragoo et al. ................ 604/378 |
| 5,575,785 | A | * | 11/1996 | Gryskiewicz et al. ... 604/385.28 |
| 5,620,431 | A | * | 4/1997 | LeMahieu et al. ....... 604/385.25 |
| 5,695,487 | A | * | 12/1997 | Cohen et al. ................... 604/384 |
| 5,906,876 | A | * | 5/1999 | Conway ........................... 428/89 |
| 6,022,338 | A | * | 2/2000 | Putzer ....................... 604/385.01 |
| 6,156,024 | A | | 12/2000 | Schulte et al. |
| 6,222,092 | B1 | * | 4/2001 | Hansen et al. ................. 604/378 |
| 6,258,997 | B1 | * | 7/2001 | Johansson et al. ............ 604/378 |

(Continued)

FOREIGN PATENT DOCUMENTS

EP 0 978 265 A2 2/2000

(Continued)

OTHER PUBLICATIONS

European search report for EP application No. 05710309.5 issued Jun. 18, 2009.

*Primary Examiner* — Tatyana Zalukaeva
*Assistant Examiner* — Susan Su
(74) *Attorney, Agent, or Firm* — Lowe, Hauptman, Ham & Berner, LLP (57) ABSTRACT

A disposable diaper has a pair of transversely opposite lateral portions in a crotch covering region. The lateral portions are provided with body fluid leak-barriers extending in a back-and-forth direction of the diaper. The leak-barriers include a plurality of strips made of a flexible sheet material. These strips are arranged side by side in the back-and-forth direction. These strips respectively have fixed portions and flexible portions.

13 Claims, 9 Drawing Sheets

U.S. PATENT DOCUMENTS

| | | | |
|---|---|---|---|
| 6,413,248 B1 | 7/2002 | Mizutani | |
| 6,482,195 B1 * | 11/2002 | Kumasaka | 604/385.27 |
| 6,521,813 B1 * | 2/2003 | Chihani | 604/384 |
| 6,706,029 B1 * | 3/2004 | Suzuki et al. | 604/385.28 |
| 6,733,610 B2 * | 5/2004 | Mizutani et al. | 156/164 |
| 6,890,327 B2 * | 5/2005 | Suzuki et al. | 604/385.28 |
| 7,172,801 B2 * | 2/2007 | Hoying et al. | 428/92 |
| 2004/0131820 A1 * | 7/2004 | Turner et al. | 428/92 |
| 2005/0182381 A1 | 8/2005 | Suzuki et al. | |
| 2005/0273073 A1 | 12/2005 | Suzuki et al. | |

FOREIGN PATENT DOCUMENTS

| | | | |
|---|---|---|---|
| EP | 1358863 A1 | | 11/2003 |
| EP | 1757256 A1 | | 2/2007 |
| JP | 2174845 A | * | 7/1990 |
| JP | 3218752 A | * | 9/1991 |
| JP | 467864 | * | 3/1992 |
| JP | 1996-322878 A | | 12/1996 |
| JP | 09-028732 A | | 2/1997 |
| JP | 928732 A | * | 2/1997 |
| JP | 1057409 A | * | 3/1998 |
| JP | 1998-192338 A | | 7/1998 |
| JP | 200245396 A | * | 2/2002 |
| JP | 2002-315776 A | | 10/2002 |
| JP | 2002-345887 A | | 12/2002 |
| JP | 2004-248769 A | | 9/2004 |
| JP | 2005-342203 A | | 12/2005 |
| WO | WO 9214429 A1 | * | 9/1992 |
| WO | WO 9515138 A1 | * | 6/1995 |
| WO | 03032882 A1 | | 4/2003 |
| WO | WO 2004058497 A1 | * | 7/2004 |

* cited by examiner

DISPOSABLE DIAPER

RELATED APPLICATIONS

The present application is based on, and claims priority under 35 U.S.C. 119(a) from, Japanese Application Number 2004-40231, filed Feb. 17, 2004, the disclosure of which is hereby incorporated by reference herein in its entirety.

BACKGROUND OF THE INVENTION

The present invention relates to a disposable diaper and more particularly to a disposable diaper effective to prevent leakage of body fluids.

There have already been proposed various means adapted to prevent bodily wastes such as loose passage and/or urine from spreading in a transverse direction of a disposable diaper and eventually leaking sideways. For example, a disposable diaper disclosed in U.S. Pat. No. 4,695,278 is provided on its inner surface and along transversely opposite side portions of the diaper with barrier cuffs for the prevention of body fluid leakage. The barrier cuffs primarily extend over a crotch covering region and extend further into front and rear waist covering regions. Each of these barrier cuffs has a proximal edge along which the barrier cuff is joined to the diaper and a distal edge extending in parallel to the proximal edge and elastically stretchable/contractible in a back-and-forth direction. Rubber threads are contractibly secured to the distal edge. With this diaper put on the wearer, the barrier cuffs are tightly placed around the wearer's thighs to prevent bodily wastes from spreading in the transverse direction and thereby to prevent sideways leakage of bodily wastes from the diaper.

However, after the barrier cuffs have been kept in close contact with the wearer under a contractile force of the rubber threads, these barrier cuffs of the prior art diaper may leave on the wearer's skin a mark of the rubber threads and/or rash.

SUMMARY OF THE INVENTION

It is an object of the present invention to provide a disposable diaper provided with leak-barrier means adapted to intercept body fluids from flowing sideways and thereby to prevent body fluids from leaking to the exterior of the diaper improved to eliminate an anxiety that such leak-barrier means might leave on the wearer's skin a mark of rubber thread and/or rash.

According to the present invention, there is provided a disposable diaper having a back-and-forth direction and a transverse direction being orthogonal to each other, the diaper comprising: an absorbent chassis including a front waist covering region, a rear waist covering region, a crotch covering region and a body fluid absorbent region locating inboard of the chassis and having a pair of lateral portions opposed to each other in the transverse direction and locating over at least the crotch covering region.

The diaper further comprises a pair of body fluid leak-barrier means provided in vicinities of the lateral portions so as to extend in the back-and-forth direction inboard of the chassis, the body fluid leak-barrier means comprising a plurality of strips formed from a flexible sheet material, the strips being arranged side by side in the back-and-forth direction while extending in the transverse direction and having fixed portions joined in the vicinities of the lateral portions and flexible portions except the fixed portions.

The diaper according to this embodiment, bodily wastes tending to flow in the transverse direction of the diaper is intercepted by the strips and thus reliably prevented from leaking out of the diaper. None of elastic members is secured in a stretched state to the strips and therefore the wearer's skin suffers from neither surface imprint nor rash due to the elastic members even after the strips have been kept in close contact with the wearer's skin.

The present invention may include the following preferred embodiments.

(1) The flexible sheet material has a cantilever stiffness in a range of 10 to 20.

(2) The strips are overlapped one on another.

According to the embodiments (1) and (2), the cantilever stiffness value described herein is the value obtained by averaging cantilever stiffness values measured in accordance with Japanese Industrial Standard (JIS) L1913 using three samples for measurement. According to this embodiment, the aforesaid advantageous effect is more enhanced.

(3) The lateral portions of the body fluid absorbent panel being let free from the opposed surface of the chassis in one of the crotch covering region, the front waist covering region and the rear waist covering region, the respective one end portions of the strips being interposed between the opposed surface and the lateral portions let free one from another and joined to one of the opposed surface or the lateral portions while the flexible portions opposed to the one end portions extend outward from the lateral portions in the transverse direction of the chassis.

According to the embodiment (3), the one end portions of the respective strips are interposed between the chassis and the lateral portions of the body fluid absorbent panel and joined to the chassis, so it is unlikely that the regions in which the one end portions are joined to the chassis might irritate the wearer's skin.

(4) Each of the strips is bent in the length direction to describe a V-shape opening outward.

According to the embodiment (4), the strips are elastically deformable so that the opening angle of the V-shape described by each of the strips may be reduced or enlarged as the diaper is put on the wearer. Consequently, there is substantially no possibility that a gap causing leakage might be left between the skin and the strips.

(5) The flexible sheet material forming the strips is a nonwoven fabric containing therein one of elastomer fibers and crimped fibers.

According to the embodiment (5), the presence of the fibers enables the strips to be elastically deformable. The strips are reliable kept in contact with the skin as the diaper having such strips is put on the wearer, because the strips can be kept in contact with the skin under the elastic deformation. In this way, leakage of body waste through the strips and the skin can be reliably prevented.

(6) A plurality of second strips independent of the body fluid leak-barrier means are arranged side by side in the transverse direction of the diaper between a pair of the body fluid leak-barrier means extending along a pair of the lateral portions to form means adapted to regulate body fluid flow forward or rearward in the back-and-forth direction.

According to the embodiment (6), the regulating means for flow of body fluids can reliably regulate flow of body fluids and therefore it is unlikely that body fluids might leak beyond the front and rear waist covering regions.

DETAILED DESCRIPTION OF THE PREFERRED EMBODIMENTS

Details of a disposable diaper according to the present invention will be more fully understood from the description given hereunder with reference to the accompanying drawings.

Figure 1:
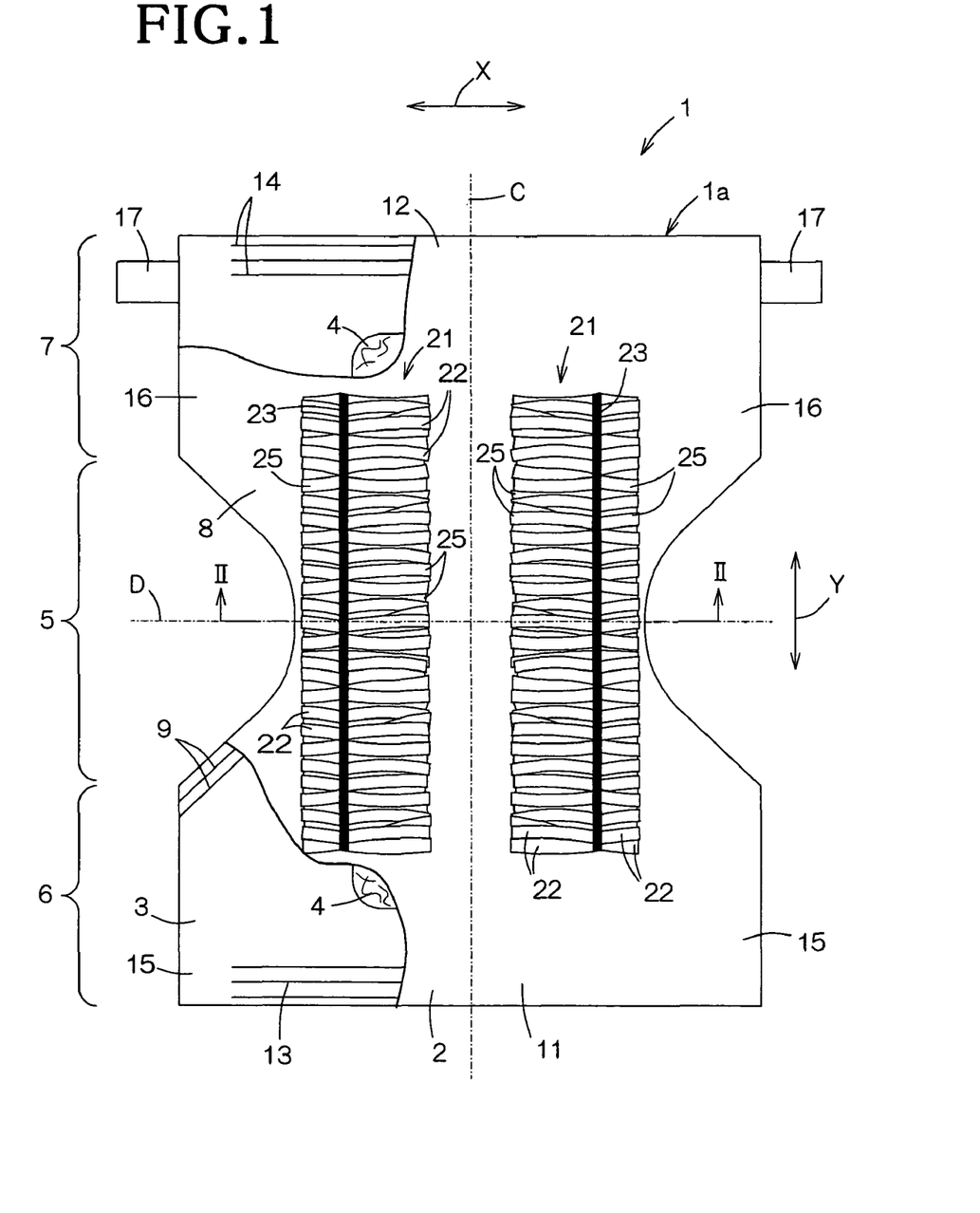
FIG. 1 is a partially cutaway plan view showing a disposable diaper as a first embodiment of the invention.

A disposable diaper 1 shown in FIG. 1 in a partially cutaway plan view is of open-type and comprises an absorbent chassis 1a having an inner sheet 2 made of a liquid-pervious nonwoven fabric, an outer sheet 3 made of a liquid-impervious plastic film and a liquid-absorbent core 4 made of liquid-absorbent materials and interposed between these sheets 2, 3. The inner and outer sheets 2, 3 extend outward beyond a peripheral edge of the core 4 and respective extensions of these sheets 2, 3 are overlapped and joined together by means of adhesive (not shown). The chassis 1a has an hourglass-like planar shape extending in a transverse direction X and a back-and-forth direction Y which are orthogonal to each other. In a middle zone of the chassis 1a as viewed in the back-and-forth direction Y, a crotch covering region 5 is defined. Front and rear waist covering regions 6, 7 are respectively defined in front of and behind the crotch covering region 5. The crotch covering region 5 has transversely opposite lateral portions describing circular arcs which are convex toward a center line C bisecting a width of the chassis 1a, i.e., a dimension of the chassis 1a in the transverse direction X and, along the transversely opposite lateral portions defining side gasket cuffs 8 (See FIG. 2), a plurality of rubber threads 9 as elastic members are interposed between the inner and outer sheets 2, 3 and contractibly secured to at least one of these sheets 2, 3 by means of hot melt adhesives (not shown). The front and rear waist covering regions 6, 7 respectively have front and rear end portions 11, 12 extending in the transverse direction X and, along these end portions 11, 12, a plurality of rubber threads as elastic members 13, 14 are interposed between the inner and outer sheets 2, 3 and contractibly secured to at least one of these sheets 2, 3 by means of hot melt adhesives (not shown). Tape fasteners 17 extend outward from transversely opposite lateral portions 16 of the rear waist covering region 7. To put the diaper 1 on the wearer, the tape fasteners 17 may be anchored on the outer sheet 3 in a vicinity of transversely opposite lateral portions 15 of the front waist covering region 6. The chassis 1a further includes a pair of body fluid leak-barrier means 21 laid symmetrically about the center line C. Each of the body fluid leak-barrier means 21 in the embodiment shown in FIG. 1 is formed from an assembly comprising a plurality of strips made of a nonwoven fabric which are laid side by side in the back-and-forth direction Y wherein these strips 22 have fixed zones 23 (See FIG. 2) fixed to the inner sheet 2 using a welding technique or appropriate adhesives. The fixed zones 23 welded to the inner sheet 2 and making the strips 22 get out of the initial shapes thereof are indicated in FIG. 1 by band-like thick lines extending in the back-and-forth direction.

Figure 2:
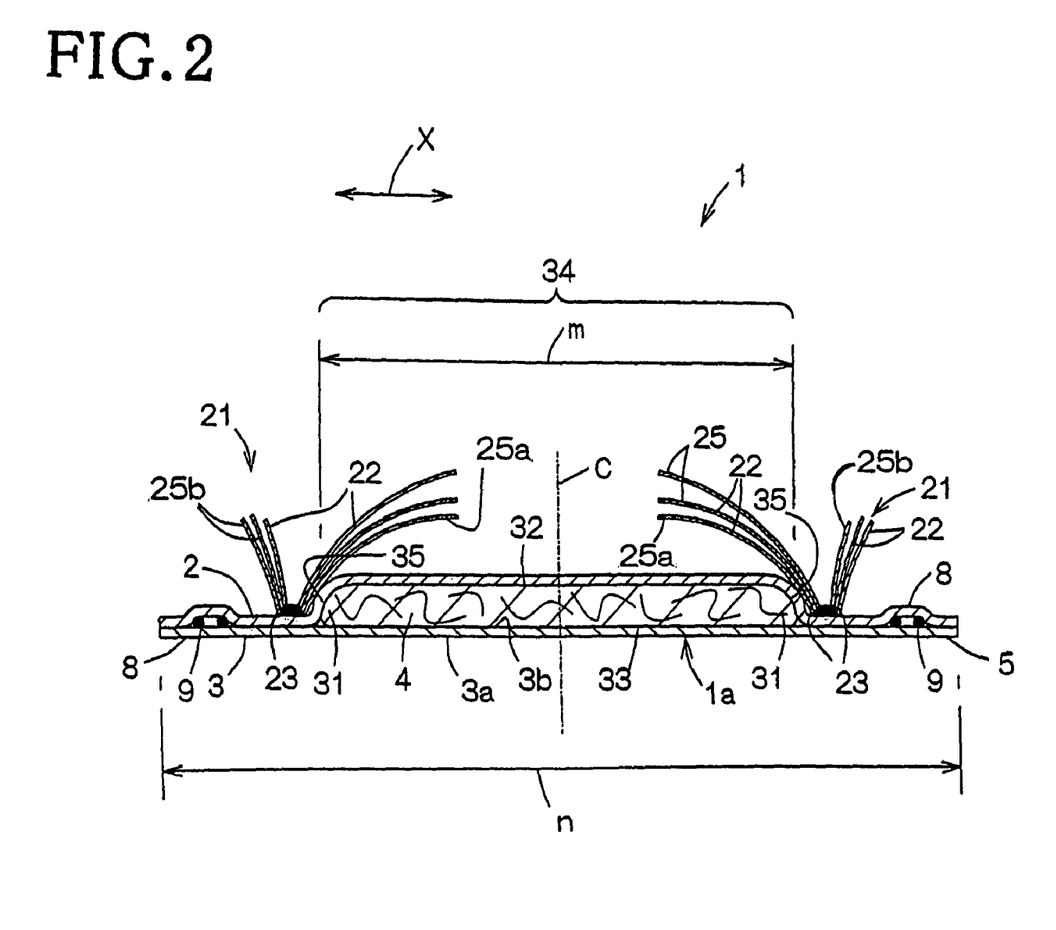
FIG. 2 is a sectional view taken along the line II-II in FIG. 1.

FIG. 2 is a sectional view taken along the line II-II corresponding to a center line D bisecting a dimension of the diaper 1 in the back-and-forth dimension. The core 4 extends in the back-and-forth direction over the crotch covering region 5 and further extends into the front and rear waist covering regions 6, 7. The core 4 has transversely opposite lateral portions 31, an inner surface 32 facing the wearer (not shown) and an outer surface 33 facing the wearer's garment. The lateral portions 31 and the inner surface 32 of the core 4 are covered with the inner sheet 2 and the outer surface 33 of the core 4 is covered with the outer sheet 3 so as to define a body fluid absorbent region 34. The body fluid absorbent region 34 has a pair of transversely opposite lateral portions 35 which are opposed to each other in the transverse direction X of the chassis 1a and extending in the back-and-forth direction Y. A dimension m between these lateral portions 35 is smaller than a width n of the crotch covering region 5 and the side gasket cuff 8 adapted to be put in close contact with the wearer's thighs extend outside the respective lateral portions 35. The chassis 1a is further provided in a vicinity of the lateral portions 35 of the body fluid absorbent region 34 with the leak-barrier means 21 comprising a plurality of the strips 22. These strips 22 each has a thickness direction corresponding to a thickness direction of the nonwoven fabric forming these strips 22, a width direction corresponding to the back-and-forth direction Y of the chassis 1a and a length direction which is orthogonal to these thickness direction and width direction. Areas of the strips 22 put aside toward one of its longitudinally opposite end portions is joined to the inner sheet 2 using a welding technique or appropriate adhesives to define the fixed portion 23 and the remaining areas extend upward and left free from the inner sheet 2 to define flexible portions 25. The flexible portions 25 are freely deformable and come in soft contact with the wearer's skin when the diaper 1 is put on the wearer. In the illustrated case, the fixed portions 23 are welded to the inner sheet 2 and consequently the strips 22 get out of the initial shapes thereof. A plurality of the strips 22 extend in the transverse direction X with the respective flexible portions 25 overlapping one another but appropriately spaced one from another in the back-and-forth direction Y of the chassis 1a and form together a flexible tuft (See FIG. 1 also). These flexible portions 25 forming together the tuft include flexible portions 25a extending obliquely upward as viewed in FIG. 2 from the lateral portions 35 of the body fluid absorbent region 34 toward the center line C and the flexible portions 25b extending upward generally in a direction orthogonal to the outer sheet 3 illustrated to be horizontal or extending obliquely upward and outward in the transverse direction X. Whether the diaper 1 is for infant or for adult, such strips 22 are preferably dimensioned so that the strips 22 each has a width in a range of 3 to 20 mm and the flexible portions 25 each has a length in a range of 10 to 80 mm. The length of each of the flexible portions 25 may be different between the case in which the flexible portions 25 extend toward the center line C and the case in which the flexible portions 25 extend outward with respect to the chassis 1a. It should be noted here that, in the case of the flexible portions 25 extending toward the center line C, their lengths are preferably dimensioned not to extend beyond the center line C as measured with the flexible portions 25 collapsed onto the inner sheet 2 and, in the case of the flexible portions 25 extending outward with respect to the chassis 1a, their lengths are preferably dimensioned not to extend beyond the lateral portion 8 and more preferably dimensioned not to extend beyond the rubber threads 9 surrounding the wearer's thigh as measured with the flexible portions 25 collapsed onto the inner sheet 2.

The nonwoven fabric as a stock material for the strips 22 is preferably selected from the group including a spun bond nonwoven fabric, a spun lace nonwoven fabric and a melt blown nonwoven fabric each having a basis weight in a range of 10 to 50 g/m². Such nonwoven fabrics preferably contain elastomer fibers or crimped fibers and are elastically deformable. While the nonwoven fabrics used for this purpose may be hydrophilic or hydrophobic, the hydrophilic nonwoven fabrics allow body fluid to be easily guided through a gap between each pair of the adjacent strips 22 to the body fluid absorbent region 34. However, it is possible without departing from the scope of the invention to form the strips 22 by a plastic film or a sheet material such as a rubber sheet or a woven fabric. It is preferable for the strips formed from such materials to be elastically deformable. The strips 22 formed from any one selected from the materials as have been described also preferably has a cantilever stiffness value in a range of 10-to 120 as measured in accordance with Japanese Industrial Standard (JIS) L 1913 and a plurality of these strips 22 also preferably can form a soft touch tuft.

As will be best seen in FIG. 1, the body fluid leak-barrier means 21 comprising a plurality of the strips 22 extend in parallel to the center line C from the crotch covering region 5 to the front and rear waist covering regions 6, 7. It should be understood here that it is possible for such body fluid leak-barrier means 21 to vary its length in the back-and-forth direction and its position, for example, to lay the body fluid leak-barrier means 21 only in the crotch covering region 5 and the rear waist covering region 7 or only in the rear waist covering region 7 or only in the front waist covering region 6.

Figure 3:
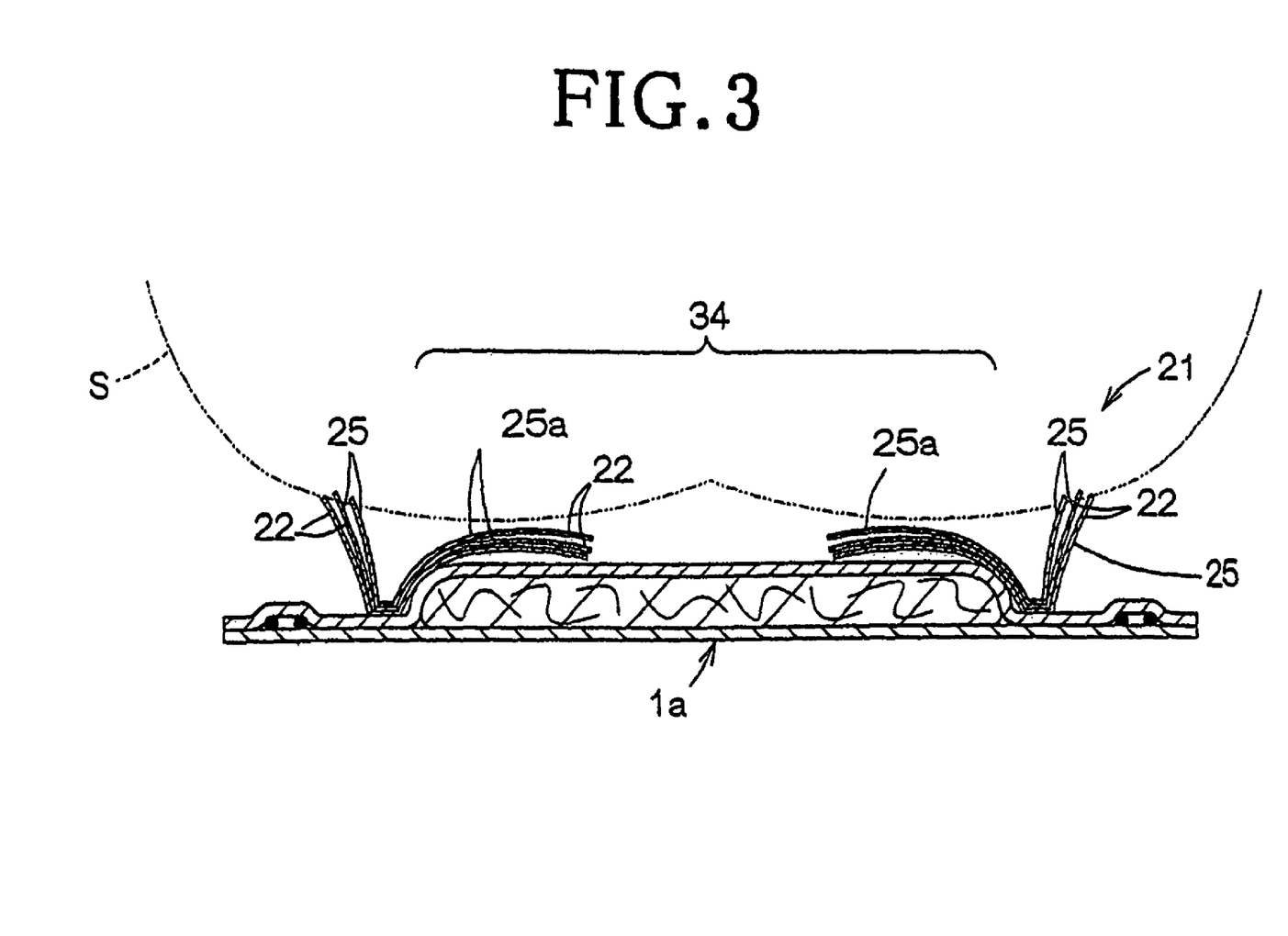
FIG. 3 is a view similar to FIG. 2, showing the disposable diaper put on the wearer.

FIG. 3 is a view similar to FIG. 2, in which the diaper 1 is put on the wearer and imaginary lines indicate the wearer's skin. The flexible portions 25 of these strips 22 are brought in contact with the skin S and thereby prevent bodily waste (not shown) from leaking beyond the strips 22 out of the diaper 1. When some of the flexible portions 25 such as those designated by reference numeral 25a in FIGS. 2 and 3 lie immediately above the body fluid absorbent region 34, the strips 22 function to prevent loose passage discharged onto the chassis 1a from spreading on the body fluid absorbent region 34 in the back-and-forth direction. As a result, there is no anxiety that the wearer's crotch and front waist regions might be soiled with loose passage.

Figure 4:
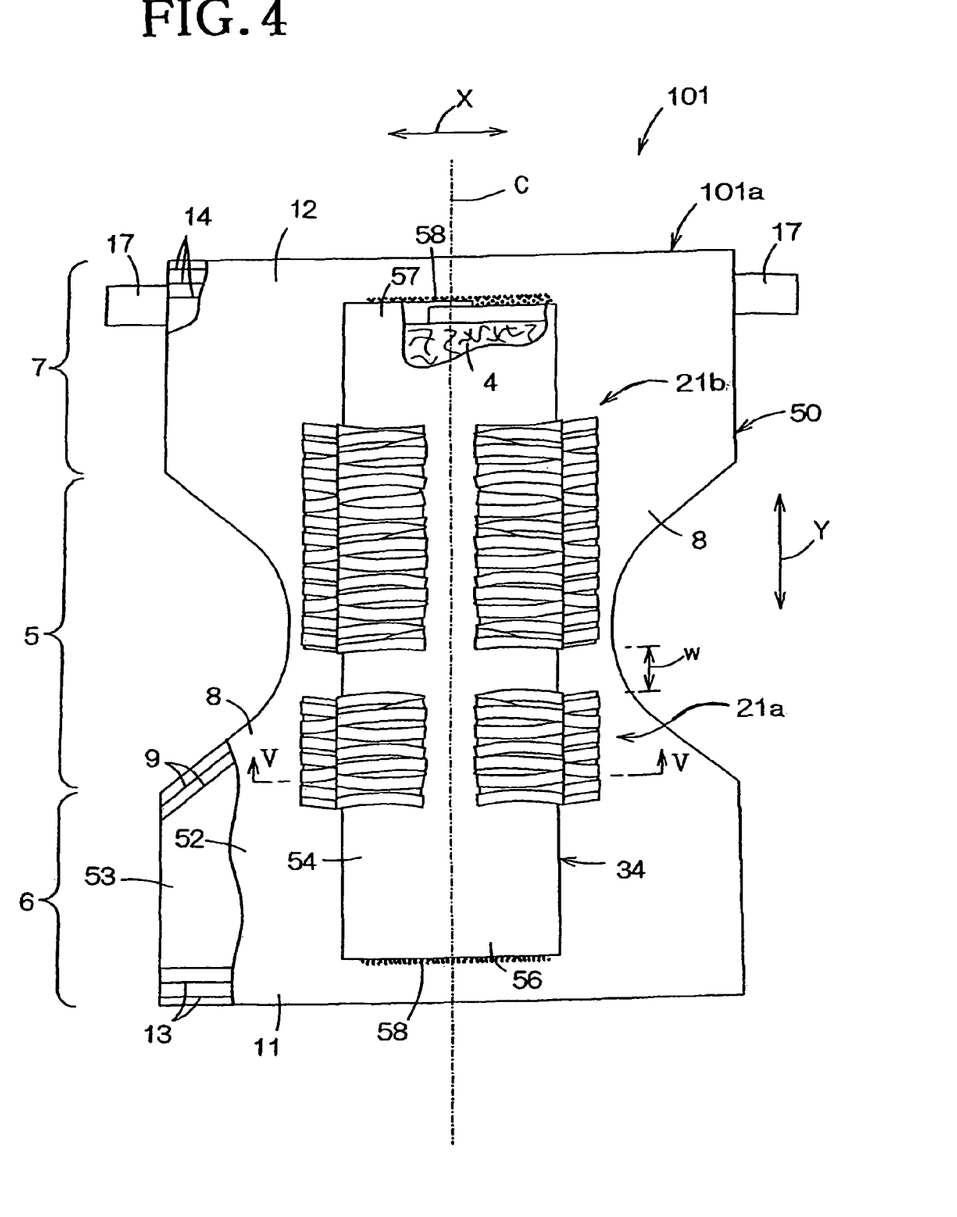
FIG. 4 is a view similar to FIG. 1, showing a second embodiment of the invention.
Figure 5:
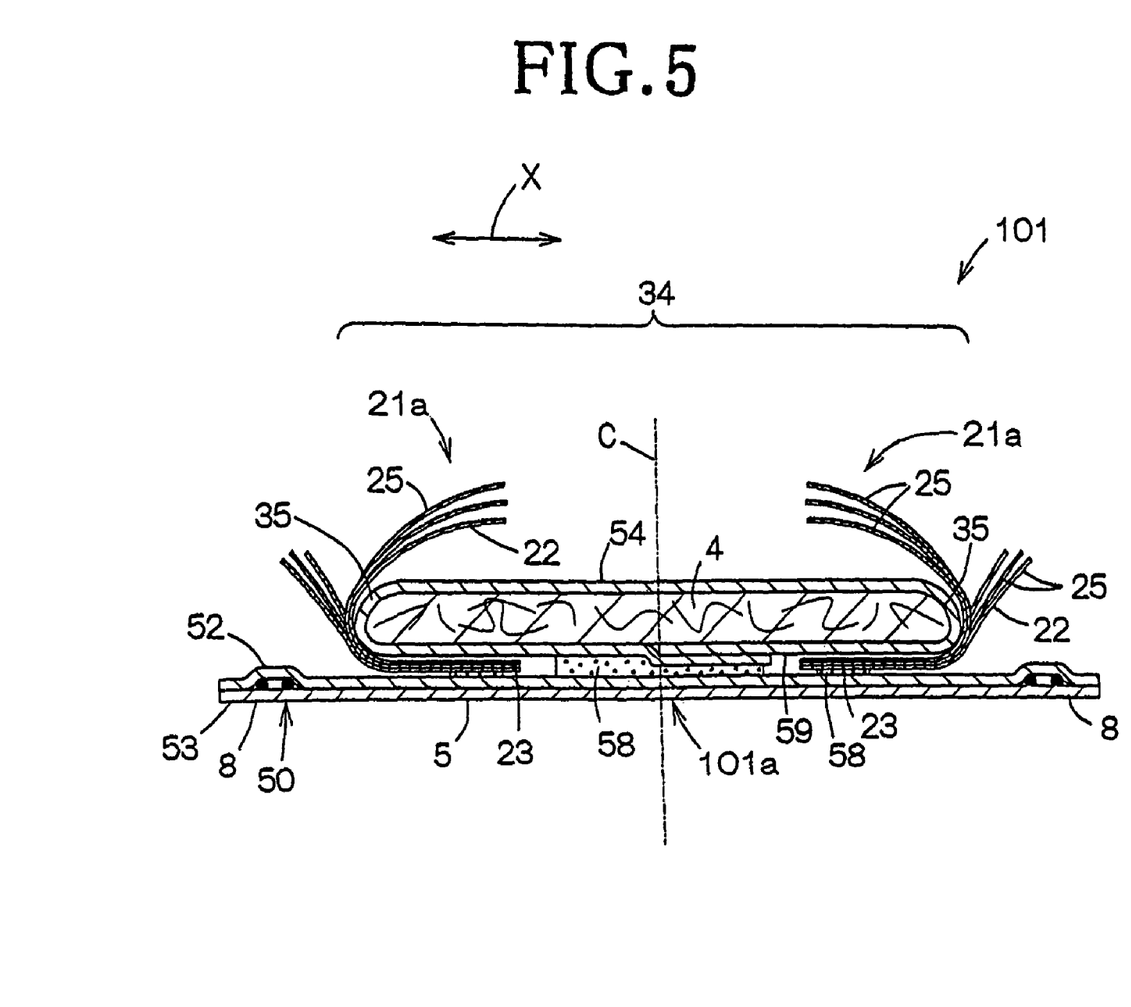
FIG. 5 is a sectional view taken along the line V-V in FIG. 4.

FIG. 4 is a view similar to FIG. 1, showing a second embodiment of the invention and FIG. 5 is a sectional view taken along the line V-V in FIG. 4. A diaper 101 according to this embodiment comprises an absorbent chassis 1a having the crotch covering region 5, the front waist covering region 6 and a rear waist covering region 7. The chassis 1a comprises the body fluid absorbent region 34 in the form of a panel having a rectangular shape which is relatively long in the back-and-forth direction Y and a base sheet 50 prepared separately of the panel.

The base sheet 50 has an inner surface defined by a liquid-impervious plastic film 52 and an outer surface defined by a nonwoven fabric 53. Transversely opposite lateral portions of the crotch covering region 5 describe circular arcs which are convex toward the center line C bisecting a dimension of the chassis 101a in the transverse direction to define the side gasket cuffs 8 destined to surround the wearer's thighs. A plurality of rubber threads 9 as the elastic members are interposed between the film 52 and the nonwoven fabric 53 along these side gasket cuffs 8 and contractibly secured to at least one of these film 52 and nonwoven fabric 53. Along the front and rear end portions 11, 12 extending in the transverse direction in the front and rear waist covering regions 6, 7, respectively, a plurality of rubber threads 13, 14 as the elastic members extending in the transverse direction x along these front and rear end portions 11, 12 are interposed between the film 52 and the nonwoven fabric 53 and contractibly secured to at least one of these film 52 and nonwoven fabric 53.

The body fluid absorbent panel 34 comprises the core 4 made from body fluid absorbent materials such as fluff pulp and super-absorbent polymer particles and a liquid-pervious sheet 54 such as a nonwoven fabric or a perforated plastic film with which the core 4 is wrapped. Front and rear end portions 56, 57 of the body fluid absorbent panel 34 are formed by upper and lower layers of the core wrapping liquid-pervious sheet 54 overlapped and joined together. These front and rear end portions 56, 57 are joined to the film 52 by means of adhesives 58. While the body fluid absorbent panel 34 is joined to the film 52 by means of adhesives 58 along a transversely middle zone of its lower surface facing the film 52 (See FIG. 5), the zone 34 is not joined to the film 52 in a vicinity of the transversely opposite lateral portions 35 of the panel 34, i.e., left free from the film 52.

In the case of this diaper 101, the leak-barrier means 21 comprises first leak-barrier means 21a extending from the crotch covering region 5 to the front waist covering region 6 of the base sheet 50 and second leak-barrier means 21b extending from the crotch covering region 5 to the rear waist covering region 7 wherein the first and second leak-barrier means 21a, 21b are spaced apart from each other in the back-and-forth direction Y by a dimension W. The first leak-barrier means 21a are formed so as to lie in a vicinity of the urethral of the wearer and the second leak-barrier means 21b are formed so as to lie in a vicinity of the anus of the wearer. Construction of the first leak-barrier means 21a is substantially similar to construction of the second leak-barrier means 21b. FIG. 5 shows a cross-sectional shape of the first leak-barrier means 21a. In the case of the first leak-barrier means 21a, the fixed zones 23 of the respective strips 22 lie under the transversely opposite lateral portions 35 of the body fluid absorbent panel 34 and fixed to the plastic film 52 using a welding technique or appropriate adhesives. In this specific embodiment illustrated by FIGS. 4 and 5, the fixed zones 23 are joined to the plastic film 52 by means of adhesives 58. The flexible portions 25 of the respective strips 22 extend from the vicinity of the transversely opposite lateral portions 35 of the body fluid absorbent panel 34 in the transverse direction X of the base sheet 50. Some of these strips 22 have the flexible portions 25 thereof curve along the transversely opposite lateral portions 35 toward the center line C and the other have the flexible portions 25 thereof extend toward the side gasket cuffs of the chassis 101a. The flexible portions 25 may be curved as in the illustrated embodiment by thermoforming the strips 22 or by joining the flexible portions 25 to the liquid-pervious sheet 54 in the vicinity of the transversely opposite lateral portions 35.

With the diaper 101 arranged as illustrated in FIGS. 4 and 5, it is unlikely that the fixed portions 23 of the respective strips 22 might come in contact with the wearer's skin and irritate it. The feature that the first and second leak-barrier means 21a, 21b are spaced apart from each other in the back-and-forth direction in the crotch covering region 5 by the dimension W allows bulkiness of the crotch covering region 5 due to the presence of the leak-barrier means to be alleviated. The dimension W is preferably in a range of 10 to 100 mm.

Figure 6:
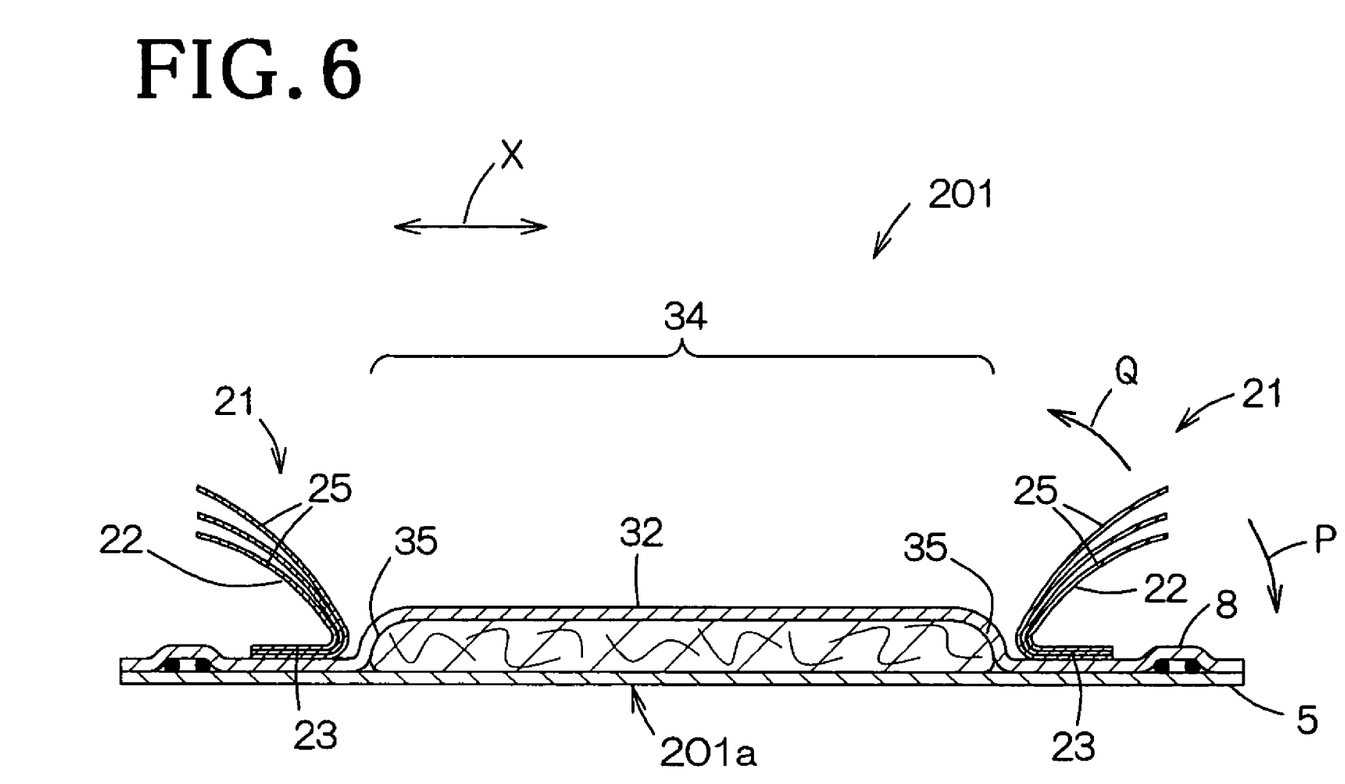
FIG. 6 is a view similar to FIG. 2, showing a third embodiment of the invention.

FIG. 6 is a view similar to FIG. 2, showing a third embodiment of the invention. In the case of a diaper 201 according to this embodiment comprising an absorbent chassis 10 similar to the chassis 1a of the diaper 1 of the first embodiment, the respective strips 22 constituting the leak-barrier means 21 are postured in a V-shape opening outward. The fixed zone 23 are joined to the side gasket cuffs 8 of the chassis 201a by means of adhesives (not shown) and the flexible portions 25 extend outward from the vicinity of the transversely opposite lateral portions 35 of the body fluid absorbent zone 34. The strips 22 come in contact with the wearer's skin (not shown) and thereby pressed down in a direction indicated by an arrow P as the diaper 201 is put on the wearer. Thereupon, a counteractive force of restoration is exerted on the strips 22 in a direction Q opposite to the direction P and thereby the strips 22 are brought in close contact with the skin substantially with no gap between the strips 22 and the skin. The strips 22 functioning in this manner are preferably made of an elastically deformable nonwoven fabric containing elastomer fibers or crimped fibers.

Figure 7:
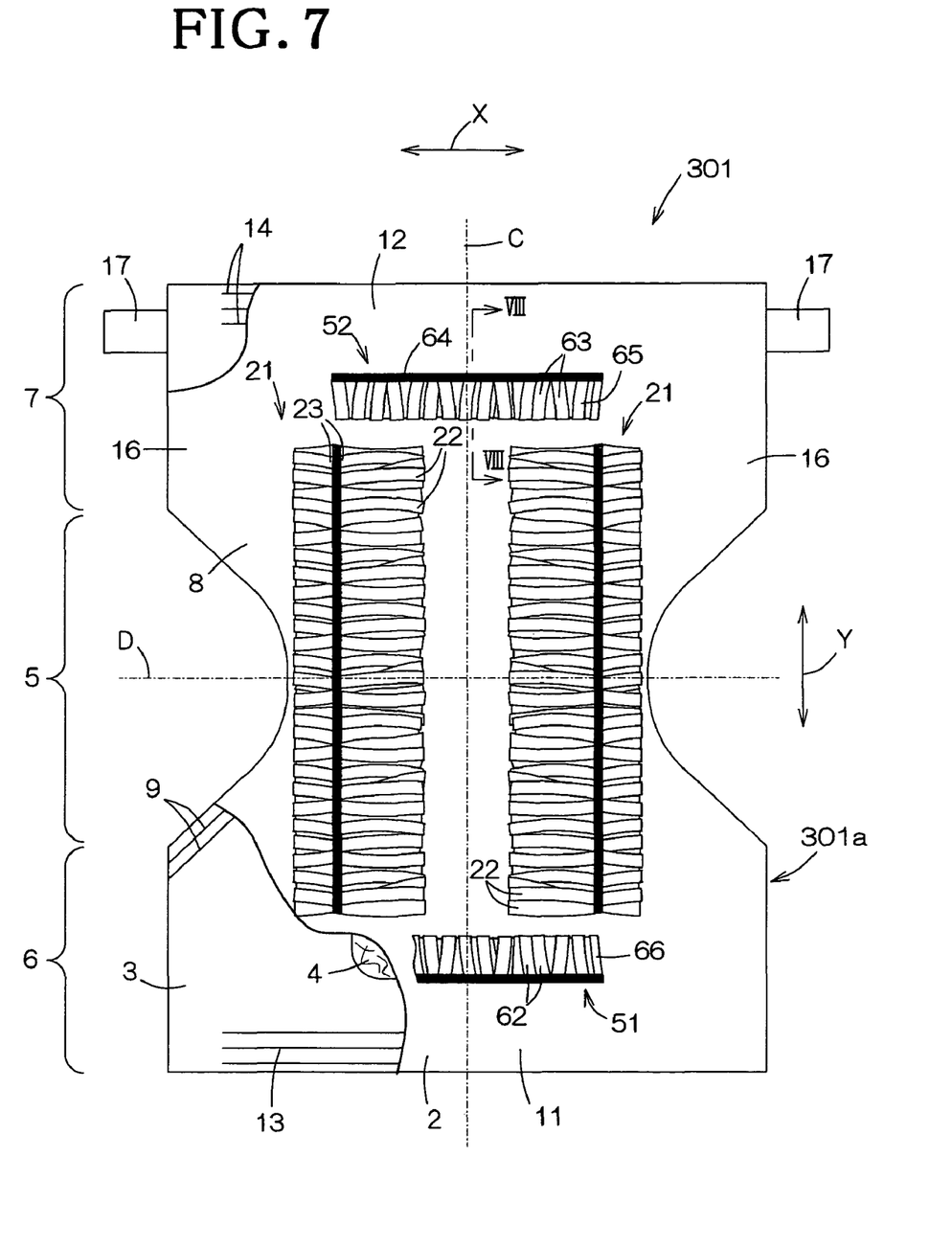
FIG. 7 is a view similar to FIG. 2, showing a fourth embodiment of the invention.
Figure 8:
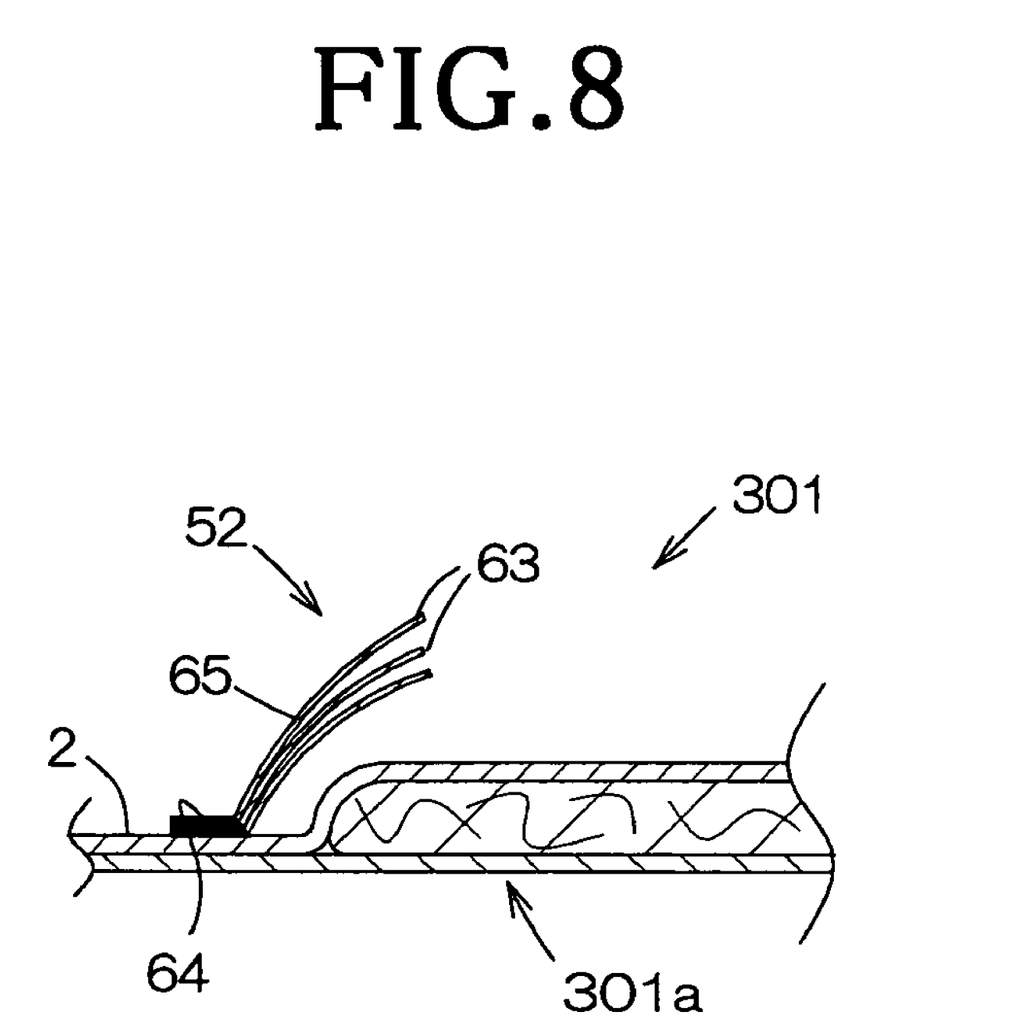
FIG. 8 is a sectional view taken along the line VIII-VIII in FIG. 7.

FIG. 7 is a view similar to FIG. 2, showing a fourth embodiment of the invention and FIG. 8 is a sectional view taken along the line VIII-VIII in FIG. 7. A diaper 301 according to this embodiment comprising an absorbent chassis 301a similar to the chassis 1a of the first embodiment of the invention includes, in addition to a pair of leak-barrier means 21 corresponding to the above described first leak-barrier means 21 each comprising a plurality of the first strips made of a nonwoven fabric similarly to the case of the first embodiment of the invention, front and rear flow regulating means 51, 52 in the front and rear waist covering regions 6, 7, respectively. These front and rear flow regulating means 51, 52 extend in the transverse direction X between the pair of leak-barrier means 21. These regulating means 51, 52 respectively comprise a plurality of second and third strips 62, 63 prepared separately of the first strips 22 and made of sheet materials such as a nonwoven fabric, a plastic film or a rubber sheet, more preferably made of an elastically deformable nonwoven fabric. These second and third strips 62, 63 are arranged side by side in the transverse direction X and extend in the back-and-forth direction with flexible portions overlapping one another. As will be apparent from FIG. 8, the third strips 63 constituting the rear flow regulating means 52 have lost the initial shapes as the strips 63 after fixed portions 64 thereof defined by proximal ends have been welded to the inner sheet 2. The flexible portions 65 defined by the end portions opposite to the fixed portions 64 extend above the inner sheet 2. In the preferred rear flow regulating means 52, the flexible portions 65 in majority of the third strips 63 extend upward obliquely or so as to describe curves toward the center line D (See FIG. 7). Construction of the front flow regulating means 51 is substantially the same as the construction of the rear flow regulating means 52 and, in the preferred front flow regulating means 51 also, the flexible portions 66 in majority of the second strips 62 extend upward obliquely or so as to describe curves toward the center line D.

The front and rear flow regulating means 51, 52 in the chassis 301a constructed in the manner as has been described above in reference with FIGS. 7 and 8 function to regulate a range in which bodily wastes (not shown) can flow on the inner sheet 2 in the back-and-forth direction. The front flow regulating means 51 is adapted to prevent body fluid from flowing forward until body fluid might leak beyond the front end portion 11 of the front waist covering region 6. The rear flow regulating means 52 is adapted to prevent body fluid from flowing rearward until body fluid might leak beyond the rear end portion 12 of the rear waist covering region 7. It should noted here that, if it is unnecessary to prevent body fluid from leaking beyond the front end portion 11 or rear end portions 12, it is possible to eliminate the front flow regulating means 51 or the rear flow regulating means 52 from the diaper 301. The second and third strips 62, 63 may be made of a good touch flexible nonwoven fabric as the first strips 22 are the case. With such strips 62, 63, there is no anxiety that visible marks or rash might be left on the wearer's skin even after these strips 62, 63 have been kept in close contact with the wearer's skin.

Figure 9:
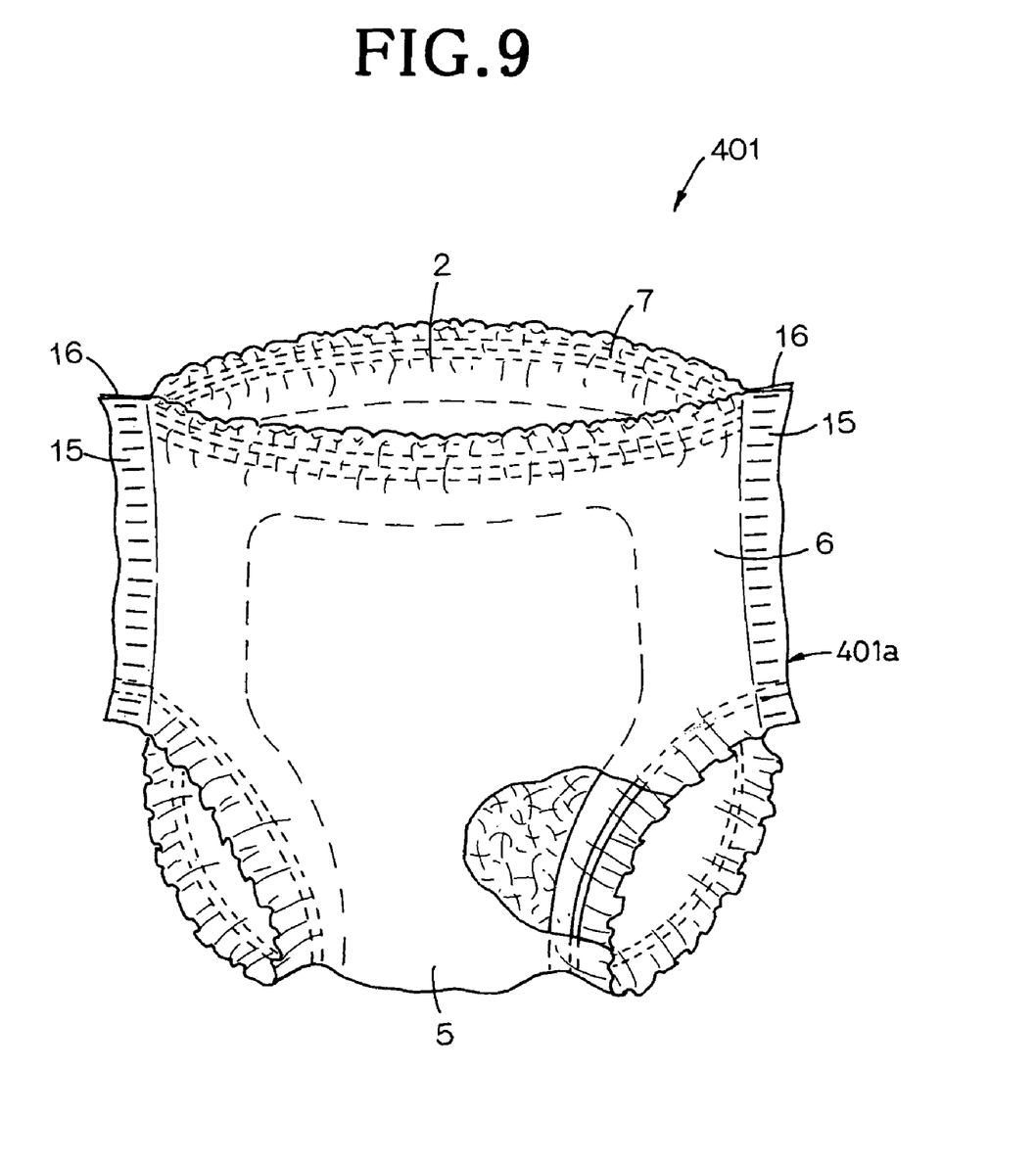
FIG. 9 is a perspective view showing a pants-type disposable diaper as a fifth embodiment of the invention.

FIG. 9 is a perspective view showing a pants-type disposable diaper 401 as a fifth embodiment of the invention comprising an absorbent chassis 301a similar to the chassis 1a of the first embodiment of the invention. Such pants-type diaper 401 may be obtained by folding the open-type diaper shown in FIG. 1 or 4 in the plan view along the center line D with the inner sheet 2 inside to put flat the transversely opposite lateral portions 15, 16 of the front and rear waist covering regions 6, 7 together, and joining these lateral portions 15, 16 to each other using adhesives or an appropriate welding technique. No tape fastener is necessary for the chassis 401a, so the tape fasteners 17 may be previously removed from the chassis when it is desired to obtain the open-type diaper as illustrated in FIG. 1 or 4.

The present invention is applicable to produce a disposable diaper provided with leak-barrier means free from the anxiety of irritating the wearer's skin.

What is claimed is:

1. A disposable diaper having a longitudinal direction and a transverse direction which are orthogonal to each other, said diaper comprising:
    an absorbent chassis including:
        opposite inner and outer surfaces, the inner surface being adapted to directly contact a wearer in use when the diaper is worn on the wearer,
        a front waist covering region,
        a rear waist covering region,
        a crotch covering region extending in the longitudinal direction between said front and rear waist covering regions, and
    a body fluid absorbent region which has a pair of transversely opposite side margins opposed to each other in said transverse direction, is located between transversely opposite side edges of said chassis, and extends at least in said crotch covering region; and
    a pair of body fluid barriers which are provided along and in vicinities of said side margins, respectively, so as to extend in said longitudinal direction, for preventing body fluid, discharged in use between said barriers, from leaking in the transverse direction beyond the barriers and out of the diaper;
    wherein
    each of said body fluid barriers comprises a plurality of strips formed from a flexible sheet material and arranged side by side in said longitudinal direction;
    each of said strips has a length in the transverse direction greater than in the longitudinal direction, is hydrophobic and includes
        a fixed portion joined to the inner surface of said chassis at a location which is positioned, in the transverse direction, outside the absorbent region and between the respective side margin of the absorbent region and a respective one of the side edges of said chassis, and
        first and second flexible portions which are formed by the remainder of the strip, are directly contactable with the wearer in use, and are located on opposite sides of said fixed portion;

wherein the first flexible portion is suspended over the body fluid absorbent region in a cantilever configuration and arranged for direct contact with the wearer in use.

2. The diaper as claimed in claim 1, wherein said flexible sheet material has a cantilever stiffness in a range of 10 to 20.

3. The diaper as claimed in claim 1, wherein adjacent said strips overlap one another.

4. The diaper as claimed in claim 1, wherein
the fixed portions of said strips are bonded directly to the inner surface of said chassis along two longitudinal bonding lines each being located, in the transverse direction, between a respective one of the side edges of said chassis and a respective one of the side margins of said absorbent region; and
the side margins of said absorbent region are positioned, in the transverse direction, between said longitudinal bonding lines.

5. The diaper as claimed in claim 4, wherein the barrier strips are free of direct attachment to the body fluid absorbent region.

6. The diaper as claimed in claim 4, wherein the flexible portions of each said barrier strip are free of direct attachment to said chassis.

7. The diaper as claimed in claim 4, wherein, in each said barrier strip, the second flexible portion is farther, in the transverse direction, from the absorbent region than the first flexible portion that is suspended over the absorbent region in a cantilever configuration.

8. The diaper as claimed in claim 7, wherein, in each said barrier strip, the second flexible portion has a length, measured in the transverse direction, smaller than that of the first flexible portion.

9. The diaper as claimed in claim 8, wherein, in each said barrier strip, said flexible portions define a V shape and diverge away from each other in the transverse direction and away from said chassis in a thickness direction of the diaper.

10. The diaper as claimed in claim 9, wherein, in each said barrier strip,
said second flexible portion extends upwardly in the thickness direction from said chassis and outwardly in the transverse direction away from said absorbent region; and
said first flexible portion extends upwardly in the thickness direction from said chassis and inwardly in the transverse direction to partially cover the respective side margin of said absorbent region.

11. The diaper as claimed in claim 4, wherein said chassis further comprises
a liquid permeable topsheet defining the inner surface of the chassis;
a liquid impermeable backsheet defining the outer surface of the chassis; and
an absorbent core sandwiched between the topsheet and the backsheet, and defining said absorbent region,
transversely opposite side edges of the absorbent core defining the side margins of said absorbent region, respectively.

12. The diaper as claimed in claim 11, wherein said flexible sheet material has a cantilever stiffness in a range of 10 to 20 and wherein adjacent said strips overlap one another.

13. The diaper as claimed in claim 12, wherein an entirety of said absorbent core is located, in the transverse direction, between the longitudinal bonding lines where the fixed portions of said strips are bonded directly to the topsheet.

* * * * *